United States Patent [19]

Klaubert et al.

[11] 4,447,611
[45] May 8, 1984

[54] BENZO-FUSED AND HETEROCYCLIC FUSED IMIDAZOLE ANTI-ULCER AGENTS

[75] Inventors: Dieter H. Klaubert, Perkiomenville; Stanley C. Bell, Penn Valley, both of Pa.

[73] Assignee: American Home Products Corporation, New York, N.Y.

[21] Appl. No.: 382,494

[22] Filed: May 27, 1982

[51] Int. Cl.³ .............................................. C07D 471/04
[52] U.S. Cl. .................................... 546/118; 546/199; 548/181; 548/303; 548/306
[58] Field of Search .................... 546/1, 199; 548/181, 548/303, 306

[56] References Cited

U.S. PATENT DOCUMENTS 4,165,378  8/1979  Gilman et al. ..................... 548/193

Primary Examiner—Henry R. Jiles
Assistant Examiner—Bernard Dentz
Attorney, Agent, or Firm—George Tarnowski

[57] ABSTRACT

Compounds of the formula

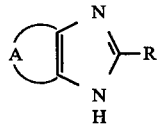

wherein A is a moiety of the formula

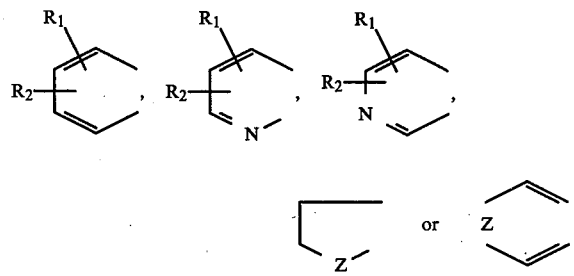

in which
$R_1$ and $R_2$ may be hydrogen, lower alkyl, lower alkoxy, halogen or thioalkyl; and
Z is O or S;
R is an amine selected from the group

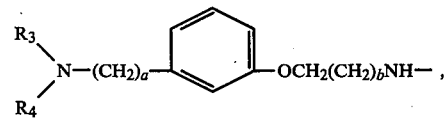

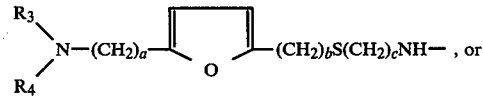

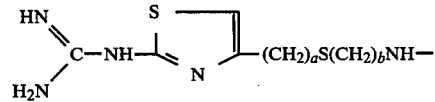

wherein
$R_3$ and $R_4$ may be hydrogen, lower alkyl, cycloloweralkyl or $R_3$ and $R_4$ taken together form an N-containing heterocycle of 2–7 carbon atoms;
$a=b=c=1-5$; and pharmaceutically acceptable salts thereof have $H_2$—antagonist activity.

The compounds can be used in the treatment of ulcers.

3 Claims, No Drawings

BENZO-FUSED AND HETEROCYCLIC FUSED IMIDAZOLE ANTI-ULCER AGENTS

This invention relates to new benzo-fused and heterocyclic fused imidazole compounds having a selective action on $H_2$ histamine receptors and which inhibit gastric acid secretion.

It has been postulated that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27, 427) and the action of histamine at this receptor is blocked (antagonized) by classical "antihistamine" drugs such as mepyramine (Pyrilamine). The second histamine receptor has been named the $H_2$ receptor (Black et al., Nature, 1972, 236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The commercialization of cimetidine and subsequent follow-up pharmacological research in pateints has demonstrated that cimetidine is a drug with limitations, such as short duration of action, anti-androgenic activity, and a tendency to cause confusional states in elderly patients. Obviously, much intensive research has been carried out to find improved $H_2$ antagonists. Indeed, selective $H_2$ antagonists having greater activity than cimetidine have been discovered. Among the better known new $H_2$ antagonists are ranitidine (disclosed in U.S. Pat. No. 4,128,658) having the structure:

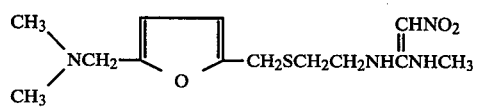

tiotidine (U.S. Pat. No. 4,165,378) having the structure:

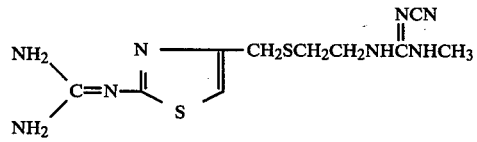

and compounds such as those disclosed in European patent application No. 24,510 having the structure:

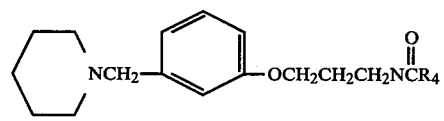

wherein $R_4$ is among others, hydrogen, methyl or methylol.

There has now been discovered a novel group of compounds, with potent $H_2$ receptor antagonist activity, having the following formula:

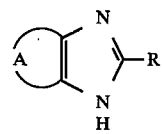

wherein A is a moiety of the formula

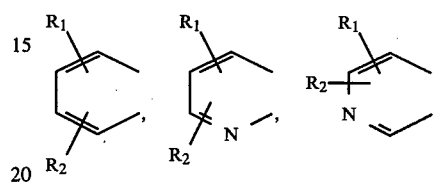

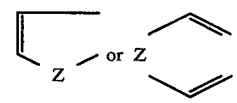

in which $R_1$ and $R_2$ may be hydrogen, lower alkyl, lower alkoxy, halogen or thioalkyl; and Z is O or S;

R is an amine selected from the group:

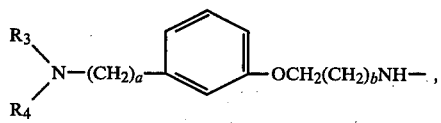

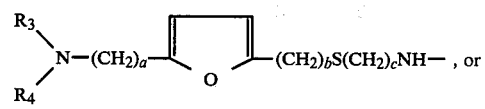

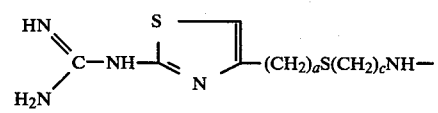

wherein $R_3$ and $R_4$ may be hydrogen, lower alkyl, cyclolower-alkyl or $R_3$ and $R_4$ taken together form an N-containing heterocyclic of 2–7 carbon atoms;

$a=b=c=1-5$; and pharmacologically acceptable salts thereof.

The term "halogen" refers to fluoro, chloro and bromo. The terms "lower alkyl" and "lower alkoxy" refer to moieties having 1–6 carbon atoms in the carbon chain.

The compounds of the invention readily form pharmacologically acceptable salts with both inorganic and organic acids, such as hydrochloric, hydrobromic, sulfuric, nitric, phosphoric, acetic, maleic, fumaric, citric, oxalic and the like.

The compounds of the invention can be readily prepared by reacting an appropriate hetero- or benzimidazolone or its chloro derivative with the desired amine according to the following reaction sequence:

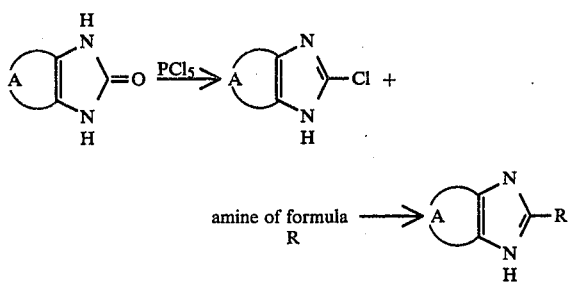

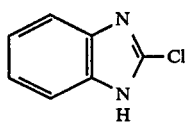

where R and A are as defined hereinbefore. The hetero- and benzo-fused imidazoles are known compounds which are readily available or which can be prepared by known methods. Thus, for example, the compound

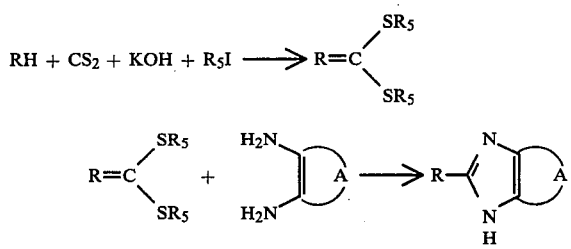

(2-chlorobenzimidazole) can be prepared according to the method of Harrison et al., *J.Chem.Soc.*, 1963, 2930-2937.

The compounds of the invention can also be prepared according to the following reaction sequence:

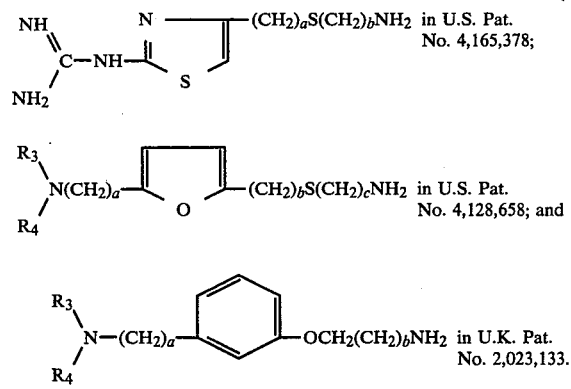

where $R_5$ is a lower alkyl, and R and A are as defined hereinbefore. In the above reaction sequences, there is first prepared a thioketene acetal which when treated with the appropriate diamine gives the desired final product.

The amines of formula R are well known in the field of $H_2$-receptor antagonists and their preparation is reported in the following patent literature:

$$\underset{NH_2}{\overset{NH}{\diagdown}}C-NH-\underset{S}{\overbrace{\phantom{xxxx}}^{N}}-(CH_2)_aS(CH_2)_bNH_2 \text{ in U.S. Pat. No. 4,165,378;}$$

$$\underset{R_4}{\overset{R_3}{\diagdown}}N(CH_2)_a-\underset{O}{\overbrace{\phantom{xxxx}}}-(CH_2)_bS(CH_2)_cNH_2 \text{ in U.S. Pat. No. 4,128,658; and}$$

$$\underset{R_4}{\overset{R_3}{\diagdown}}N-(CH_2)_a-\overbrace{\phantom{xxxx}}-OCH_2(CH_2)_bNH_2 \text{ in U.K. Pat. No. 2,023,133.}$$

The compounds of the invention have potent histamine blocking activity and can be used in the treatment of conditions where there is hypersecretion of gastric acid, such as in gastric and peptic ulceration, and other conditions caused or exacerbated by gastric acidity such as stress ulceration or gastric intestinal bleeding due to trauma.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 g per day, in the form or dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The histamine $H_2$-antagonist activity of the compounds of the invention may be demonstrated by the ability of the compounds to inhibit the histamine-induced positive chronotropic response in the spontaneously beating right atrium of the guinea pig heart, as well as by activity in other more generalized procedures, such as the modified Shay procedure of pylorus ligation for the study of rat gastric secretion. The procedures for the results of these tests are presented at the end of the following examples, which will serve to illustrate the present invention.

Preparation A

Preparation of 2-chlorobenzimidazole

Following the procedure of Harrison et al., *J.Chem.Soc.*, 1963, 2930-2937, 15 g benzimidazolin-2-one is boiled under reflux for $3\frac{1}{2}$ hours with 150 ml phosphoryl chloride, dry hydrogen chloride being passed through the refluxing mixture for the last three hours of the reaction. The excess phosphoryl chloride is removed at about 40 mm and the residue treated with about 40 ml of ice water. The cold acid solution is filtered, and the insoluble unreacted benzimidolin-2-one is washed with dilute hydrochloric acid, then with water. The filtrate and washings are made just alkaline, as determined by a litamus test, by the addition of dilute ammonia solution. After thorough cooling, crude 2-chlorobenzimidazole is collected, washed with water and dried. The reaction sequence yields 0.5 g of unreacted benzimidazolin-2-one and 15.6 g of title compound which has a m.p. of 180° C. (softens, bubbles, then resolidifies).

Analysis for: $C_7H_5ClN_2$, Calculated: C, 55.1; H, 3.3; Cl, 23.2; N, 18.4, Found: C, 55.1; H, 3.4; Cl, 23.2; N, 18.4.

EXAMPLE 1

2-[3-[3-(1-piperidinylmethyl)phenoxy]propylamine]-benzimidazole, oxalate

A mixture of 2.45 g (10 mmol) of 3-[3-(1-piperidinylmethyl)phenoxy]propylamine and 1.52 g (10 mmol) of 2-chlorobenzimidazole, prepared as in Preparation A above, in 60 ml of ethanol is heated in a sealed vessel at 150° C. for 26 hours. Evaporation and chromatographic purification yield the desired compound, which is converted to the oxalate salt with oxalic acid in ethanol. M.p. 195°–200° C. (dec.)

Analysis for: $C_{22}H_{28}N_4O_2C_2H_2O_2$, Calculated: C, 57.34; H, 5.92; N, 10.28, Found: C, 57.61; H, 6.07; N, 10.18.

EXAMPLE 2

2-[3-[3-(1-piperidinylmethyl)phenoxy]-propylamine]imidazopyridine

A. Ketenimine thioacetel of 3[3-(1-piperidinylmethyl)phenoxy]propylamine

To 2.5 g (60 mmol) of 3[3-(1-piperidinylmethyl)-phenoxy]propylamine in 25 ml ethanol at 0° C. is added 4.6 g carbon disulfide and the reaction mixture is stirred 20 minutes, after which there is added 1.1 g (20 mmol) of potassium hydroxide in 5 ml ethanol, and the mixture is stirred for 1 hour at 0° C., after which there is added 3.6 g (25 mmol) of methyl iodide in 10 ml ethanol. The mixture is stirred at 0° C. for 1 hour and then at 25° C. for 2 hours. The reaction mixture is filtered through celite, the solvent is removed, the residue dissolved in ether, filtered and the solvent removed to yield 3.5 g of an oil.

B. 2-[3-[3-(1-piperidinylmethyl)phenoxy]-propylamine]imidazopyridine 352 mg (1 mmol) of the ketenimine thioacetel of A above and 109 mg of 2,3-diaminopyridine are refluxed for 4 hours in acetonitrile. After this time, the reaction mixture is evaporated to dryness, 10 ml of dimethylformamide are added and the mixture is heated to 120° C. for 1 hour. The mixture is then evaporated to dryness, and the residual material is chromatographed on silica gel with methylene chloride/methanol/ammonium hydroxide to yield the title compound.

EXAMPLE 3

The guinea pig heart atrium test is carried out as follows:

A guinea pig right atrium is suspended at 1 g. tension (isometric) in a thermostatically controlled (32° C.) tissue bath (10 ml) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant ($pA_2$) of the $H_2$ antagonist as determined by standard procedures. Cimetidine is used as the standard for this test.

The results of this test are as follows:

| Compound | $pA_2$ Value |
|---|---|
| Cimetidine | 6.5 |
| 2-[3-[3-(1-piperidinylmethyl)phenoxy]propylamine]benzimidazole | 7.1 |

The results show that the compound is a highly active $H_2$ antagonist, being significantly more active than the standard compound cimetidine.

EXAMPLE 4

The procedure for testing gastric secretion in the rat, a modification of the procedure of Shay et al., *Gastroenterology*, 26, 906–13 (1954) is carried out as follows:

Male Charles River rats weighing 200–300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml. of gastric juice is titrated with 0.1 N NaOH to a pH of 7.0–7.4 Titratable acid output is calculated in microequivalents and the percent inhibition of acid output is calculated as follows:

$$\% \text{ Inhibition of Acid Output} = \frac{\text{Acid Output (control)} - \text{Acid Output (Drug)}}{\text{Acid Output (control)}} \times 100$$

The test result for the compound 2-[3-[3-[(1-piperidinylmethyl)]phenoxy]propylamine]benzimidazole (A) is as follows:

| Compound | Dose (mg/kg) | % Inhibition |
|---|---|---|
| A | 32 | 65 |

The results show the compound of the invention to have significant activity in inhibiting gastric acid secretion.

What is claimed is:
1. A compound having the formula

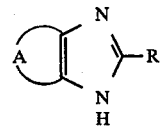

wherein A is a moiety of the formula

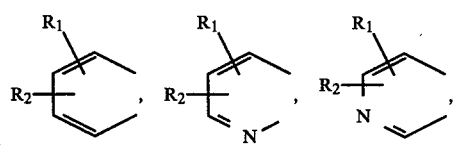

-continued

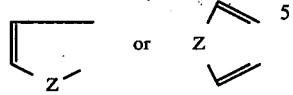 or in which

R₁ and R₂ may be hydrogen, lower alkyl, lower alkoxy, halogen or thioalkyl; and

Z is O or S;

R is an amine selected from the group

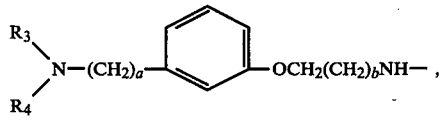

-continued

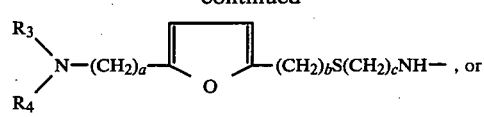

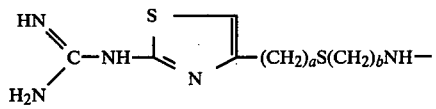

wherein

R₃ and R₄ may be hydrogen, lower alkyl, cyclolower-alkyl or R₃ and R₄ taken together form a piperidinyl ring;

a=b=c=1-5; and pharmaceutically acceptable salts thereof.

2. The compound of claim 1, which is 2-[3-[3-(1-piperidinylmethyl)phenoxy]propylamine]benzimidazole.

3. The compound of claim 1, which is 2-[3-[3-(1-piperidinylmethyl)phenoxy]propylamine]imidazo-pyridine.

* * * * *